(12) United States Patent
Wohlfahrt et al.

(10) Patent No.: US 9,791,330 B2
(45) Date of Patent: Oct. 17, 2017

(54) DEVICE AND METHOD FOR MEASURING A CHANGE IN LENGTH OF A SAMPLE AND/OR FOR MEASURING A DEFORMATION FORCE ON A SAMPLE

(71) Applicant: NETZSCH-GERÄTEBAU GMBH, Selb (DE)

(72) Inventors: Fabian Wohlfahrt, Selb (DE); Thomas Denner, Selb (DE); Georg Storch, Selb (DE)

(73) Assignee: Netzsch-Gerätebau GmbH, Selb (DE)

( * ) Notice: Subject to any disclaimer, the term of this patent is extended or adjusted under 35 U.S.C. 154(b) by 261 days.

(21) Appl. No.: 14/626,328

(22) Filed: Feb. 19, 2015

(65) Prior Publication Data
US 2015/0233775 A1   Aug. 20, 2015

(30) Foreign Application Priority Data

Feb. 19, 2014   (DE) .......................... 10 2014 102 077

(51) Int. Cl.
| | | |
|---|---|---|
| *G01N 3/08* | (2006.01) | |
| *G01N 3/20* | (2006.01) | |
| *G01N 3/24* | (2006.01) | |
| *G01L 1/04* | (2006.01) | |
| *G01N 19/00* | (2006.01) | |

(52) U.S. Cl.
CPC ................ *G01L 1/04* (2013.01); *G01N 19/00* (2013.01)

(58) Field of Classification Search
CPC . G01L 1/04; G01N 19/00; G01N 3/08; G01N 3/20; G01N 3/24; G01N 2203/0017

USPC ....... 73/862.621, 862.49, 962.392, 818, 826, 73/811
See application file for complete search history.

(56) References Cited

U.S. PATENT DOCUMENTS 5,154,085 A * 10/1992 Takeda ..................... G01N 3/38
374/47
5,915,283 A   6/1999 Reed et al.
(Continued)

FOREIGN PATENT DOCUMENTS

| | | |
|---|---|---|
| DE | 69724021 T2 | 6/2004 |
| DE | 10206710 B4 | 4/2007 |
| JP | H01274033 A | 11/1989 |

OTHER PUBLICATIONS

European Search Report Application No. 15000191.5 dated Jul. 1, 2015; dated Jul. 9, 2015 5 Pages.

*Primary Examiner* — Laura Martin
*Assistant Examiner* — Suman K Nath
(74) *Attorney, Agent, or Firm* — Whitmyer IP Group LLC

(57) ABSTRACT

A system for measuring change in length and/or deformation force on a sample in a longitudinal direction. The system is useful in thermomechanical analysis and/or dynamic-mechanical analysis, and comprises a pushrod extending in the longitudinal direction which exerts force on the sample, and a device measuring movement of the pushrod resulting from the change in length or deformation of the sample in the longitudinal direction. The measuring device includes: a pushrod base mounted on a stationary base with a guide so as to be movable in the longitudinal direction; a controllable drive for moving the pushrod; a detector measuring the force exerted by the pushrod on the sample; and a path sensor for measuring the movement of the pushrod.

11 Claims, 12 Drawing Sheets

(56) References Cited

U.S. PATENT DOCUMENTS

| | | | | |
|---|---|---|---|---|
| 7,258,022 B2* | 8/2007 | Wenski | ................... | G01N 3/08 |
| | | | | 73/800 |
| 2003/0188585 A1* | 10/2003 | Esser | ..................... | G01N 3/08 |
| | | | | 73/826 |
| 2005/0132782 A1* | 6/2005 | Wallevik | ................ | B01F 7/063 |
| | | | | 73/54.28 |
| 2007/0278054 A1* | 12/2007 | Huss | ..................... | B65H 59/22 |
| | | | | 188/161 |

* cited by examiner

DEVICE AND METHOD FOR MEASURING A CHANGE IN LENGTH OF A SAMPLE AND/OR FOR MEASURING A DEFORMATION FORCE ON A SAMPLE

FIELD OF THE INVENTION

The present invention relates to a device and a method for measuring a change in length of a sample and/or for measuring a deformation force on a sample, in particular for use in a thermomechanical analysis, also referred to hereinafter as "TMA", or for use in a dynamic-mechanical analysis, also referred to hereinafter as "DMA".

BACKGROUND OF THE INVENTION

The TMA determines dimensional changes of a sample (e.g. solid, liquid or pasty material) as a function of the temperature and/or time under defined mechanical loading.

The DMA determines a deformation force on a sample as a function of the temperature and/or time under defined dynamic-mechanical deformation.

The "deformation force" and the "deformation" can be measured and processed as such, i.e. understood as a force or a path (by which the sample is deformed). In connection with a standard DMA "in the narrower sense", wherein the sample is subjected to a deformation (deformation path) changing sinusoidally with time, the "deformation force" and the "deformation" can on the other hand also be characterised by a "force amplitude" (of the sinusoidally varying deformation force) or "path amplitude" (of the sinusoidally varying deformation path).

TMA and DMA can for example provide valuable information concerning properties, composition, structure, production conditions and possible uses of materials.

As a typical area of use of TMA, the characterisation of plastics (e.g. elastomers), paints and lacquers, composite materials, adhesives, films, fibres, ceramics, glasses and metals may be mentioned merely by way of example.

DMA can for example be used to determine viscoelastic material properties (moduli, loss factor, attenuation etc.) or temperatures which characterise the elastic or viscoelastic behaviour of a material.

Apart from the already mentioned use for TMA and DMA, the invention can for example also be used for so-called relaxation measurements, wherein a deformation force on a sample is measured and recorded as a function of temperature and/or time under defined, in particular for example constant, mechanical deformation loading.

Although a wide variety of devices and methods of the type mentioned at the outset are known in the prior art, a need for improvements to such devices and methods, for example with regard to the performance of the most precise possible measurements with a straightforward and reliable design, continues to exist in practice, especially for use with TMA and/or DMA.

SUMMARY OF THE INVENTION

It is a problem of the present invention to provide a device and a method of the type mentioned at the outset, by means of which it is possible, in particular in a straightforward, reliable and precise way, to measure the change in length of a sample with at the same time force loading that can be preselected in a well defined manner and/or the deformation force on a sample with at the same time a deformation that can be preselected in a well defined manner.

According to a first aspect of the invention, this problem is solved by a device for measuring a change in length of a sample force-loaded in a predetermined manner in a direction, referred to hereinafter as the longitudinal direction, with a pushrod extending in the longitudinal direction, which exerts the predetermined force on the sample with an end of the pushrod during the measurement, and with a measuring device by means of which, during the measurement, the movement of the pushrod resulting from the change in length of the sample in the longitudinal direction is measured, wherein the measuring device comprises:

a stationary base, a pushrod base mounted on the stationary base by means of a guide device so as to be movable in the longitudinal direction relative to the stationary base, to which pushrod base the pushrod can be or is fixed, a controllable drive device for driving the pushrod base in the longitudinal direction relative to the stationary base (for the adjustment of the predetermined force), a force measuring device for detecting the force exerted by the pushrod on the sample, a path sensor for measuring the movement of the pushrod in the longitudinal direction relative to the base, and a control device, which is designed to control the drive device depending on the force detected by means of the force measuring device according to the predetermined force loading.

This device, which can be used in particular in a TMA device, can be advantageously designed in a relatively straightforward manner, wherein a high degree of precision is also achieved both with regard to the predetermined force loading as well as the measured change in length.

Regarding the term "predetermined force loading", it should be noted that this can in principle relate both to tensile force loading as well as to compressive force loading that is exerted by means of the pushrod on the sample concerned.

In the simplest case, it involves a constant force, which is kept constant, for example in case of a TMA, over the entire temperature range passed through or over the entire duration of the TMA. Diverging from this, however, the force loading can also represent a force varying with time.

Finally, it should be noted that the force exerted on the sample according to the predetermined force loading can in principle be arbitrarily small (within what is technically feasible). To this extent, the device can be used not only particularly advantageously for the TMA "in the narrower sense", in which an "appreciably large" force loading occurs (e.g. with values of more than 0.5 N, in particular more than 1 N, for example approx. 3-5 N, being reached operationally), but also for so-called "dilatometry", wherein the change in length of a sample is ascertained in the narrower sense under negligible force loading (e.g. force of at most 0.5 N).

The term thermomechanical analysis or TMA used here can in this regard be understood in general fashion, dilatometry also being included as a special case.

Moreover, the fact should not be excluded that in the measurement, apart from the length or change in length of the sample concerned, one or more other physical properties are detected on the sample and recorded as a function of time, preferably together with the sample length or change in sample length.

In an embodiment, the force exerted by the pushrod on the sample is detected with a resolution of at most 10 mN, in particular at most 1 mN.

In an embodiment particularly suitable for dilatometry (in the narrower sense), the force, which is operationally adjustable or adjusted during the measurement, is greater than 50 mN, in particular greater than 100 mN, but on the other hand less than 1 N, in particular at most 0.5 N.

In an embodiment particularly suitable for TMA (in the narrower sense), the force, which is operationally adjustable or adjusted during the measurement, is greater than 5 mN, in particular greater than 10 mN, but on the other hand less than 10 N, in particular at most 5 N.

In an embodiment, the control device is designed, according to an operating mode, to provide a constant force loading of the sample throughout the entire measurement.

In an embodiment, the control device is designed, according to a (possibly different) operating mode, to provide a variable force loading of the sample during the measurement. The latter can for example be very advantageous for the measurement of the change in length of a sample "undergoing modulated force-loading" in a "force modulated TMA", because the sample can thus be characterised in a more detailed manner.

In a use in the context of a TMA, provision can be made for example such that a temporally periodic force (e.g. with a ramped, sinusoidal, triangular or rectangular or pulsed course) is preselected according to an operating mode, wherein the period of such a force modulation can in particular be, for example, much shorter than the TMA measurement duration (within which the sample runs through a "temperature program" which is preselected for example by the operator).

In an embodiment intended for a "(periodically) force-modulated TMA", the force modulation frequency lies in a range from 0.0001 Hz to 4 Hz, in particular 0.0002 Hz to 2 Hz.

In an embodiment, the measurement duration of the TMA lies in a range from 15 min to 40 h, in particular 30 min to 30 h.

According to a second aspect of the invention, the problem posed at the outset is solved by a device for measuring a deformation force on a sample deformed in a predetermined manner in a direction, referred to hereinafter as the longitudinal direction, with a pushrod extending in the longitudinal direction, which brings about the predetermined deformation of the sample with an end of the pushrod during the measurement, and with a measuring device by means of which, during the measurement, the deformation force accompanying the deformation of the sample in the longitudinal direction is measured, wherein the measuring device comprises:
  a stationary base,
  a pushrod base mounted on the stationary base by means of a guide device so as to be movable in the longitudinal direction relative to the stationary base, to which pushrod base the pushrod can be or is fixed,
  a controllable drive device for driving the pushrod base in the longitudinal direction relative to the stationary base (for the adjustment of the predetermined deformation),
  a force measuring device for detecting the force exerted by the pushrod on the sample,
  a path sensor for measuring the movement of the pushrod in the longitudinal direction relative to the base, and
  a control device (ST), which is designed to control the drive device depending on the movement detected by means of the path sensor according to the predetermined deformation.

This device, which can be used in particular in a DMA device or a device for performing relaxation measurements, differs from the device described above usable for TMA or dilatometry by the "control device" or the manner of processing "sensor signals" (of the force measuring device or the path sensor) in order to generate the "actuator signal" (for the drive device).

Against this background, it is even conceivable by means of the invention to provide a device with all the features of the device according to the first aspect of the invention and all the features of the device according to the second aspect of the invention, in order for example to obtain a device which can be used both for TMA or dilatometry as well as for DMA. For this purpose, the control device merely has to be designed to control the drive device in a "first operating mode" depending on the force detected by means of the force measuring device according to the predetermined force loading, and in a "second operating mode" depending on the movement detected by means of the path sensor according to the predetermined deformation.

However, since operating parameters important in practice, such as the size of the force loading or deformation loading to be exerted on the sample and a possible modulation frequency of the force loading or deformation loading, usually have to be selected differently for TMA and dilatometry on the one hand and DMA on the other hand, the creation of a device optimised for TMA or optimised for DMA is preferred.

With the device according to the second aspect of the invention, according to an embodiment the "deformation" is the amplitude of a deformation path which changes sinusoidally with time and is brought about by means of the pushrod (together with the frequency of this deformation change), and the "deformation force" is the amplitude of a deformation force correspondingly changing sinusoidally with time and transmitted by means of the pushrod (preferably together with the phase shift in respect of the deformation).

In a simple case, the predetermined deformation is a sinusoidally varying deformation path with a frequency and an amplitude, which in a DMA, for example, are kept constant over the entire temperature range passed through or over the entire duration of the DMA.

In an embodiment, the control device is accordingly designed to provide, according to an operating mode, a constant deformation of the sample throughout the entire measurement. Especially in a DMA measurement, "constant deformation" can mean a constant amplitude of a periodically (e.g. sinusoidally) changing deformation path. A "constant deformation" in the sense of a constant deformation path is however also conceivable, such as for example in a relaxation measurement, in which the deformation force on the sample is measured and recorded as a function of the temperature and/or time under defined constant mechanical deformation loading.

Diverging from this, however, the predetermined deformation can also be provided with a path frequency varying with time and/or a path amplitude varying with time.

In an embodiment, the control device is accordingly designed to provide, according to a (possibly different) operating mode, a variable deformation of the sample throughout the entire measurement. Especially in a DMA measurement, "variable deformation" can mean a variable amplitude of a periodically (e.g. sinusoidally) changing deformation path. A "variable deformation" in the sense of a variable deformation path is however also conceivable, such as for example in a relaxation measurement, in which the deformation force on the sample is measured and recorded as a function of the temperature and/or time under defined variable mechanical deformation loading.

As in the case of the TMA, it should not be excluded within the scope of the invention also in the case of a DMA (or for example a relaxation measurement) that, apart from the deformation force on the sample concerned, one or more other physical properties are detected on the sample during the measurement and preferably recorded together with the deformation force as a function of time.

In an embodiment particularly suitable for the DMA, an operationally adjustable deformation path amplitude or a deformation path amplitude adjusted during the measurement (for a periodically, in particular for example sinusoidally varying deformation path) is greater than 10 nm, in particular greater than 100 nm, but on the other hand less than 5 mm, in particular at most 0.5 mm.

In an embodiment, the force detected by the force measuring device is processed with a resolution of at most 2 mN, in particular at most 1 mN.

In an embodiment, the control device is designed to provide, according to a DMA operating mode, a sinusoidally varying deformation path with a deformation path frequency constant over the entire measurement.

In an embodiment, the control device is designed to provide, according to a (possibly different) DMA operating mode, a sinusoidally varying deformation path with a deformation path frequency varying over the measurement.

The deformation path frequency can lie for example in a range from 0.005 Hz to 1000 Hz, in particular 0.01 Hz to 100 Hz.

In an embodiment, the measurement duration of the DMA lies in a range from 10 min to 15 h, in particular 30 min to 4 h.

Within the scope of the invention, the guide device is used to provide a mounting for the pushrod base (to which the pushrod can be or is fixed), in such a way that the pushrod base can be moved in the longitudinal direction relative to the stationary base. As a result of this movement, the predetermined force is exerted on the sample or the predetermined deformation of the sample is brought about.

There are various possibilities for the structural embodiment of the guide device. The guide device particularly preferably functions according to a principle, as is known from the prior art, of so-called "linear guides".

In particular, the guide device can comprise for this purpose at least one "guide rail" (in particular guide profile), which extends linearly in the longitudinal direction and is constituted on the base or rigidly connected, e.g. screwed, to the base, on which guide rail a "guided part", usually referred to as a "carriage", is guided.

This guide in the longitudinal direction can for example involve, in a manner known per se, a sliding friction between the carriage and the guide rail (mutually corresponding profile contours of the carriage and the guide rail). Alternatively or in addition, roller bearings (e.g. ball bearings or needle bearings etc.) can be used between the guide rail and the carriage.

The particular advantage of the embodiment of the guide device according to this "linear guide" principle, i.e. for example as an arrangement of one or more (parallel running) linear guide devices known per se within the scope of the invention, consists in the fact that this principle is basically not limited with regard to the length over which the guide device supports the pushrod base in a movable manner relative to the stationary base, referred to hereinafter as the "guide stroke", and to this extent advantageously enables particularly long traversing paths.

A further advantage of this principle consists in the fact that, on account of the guide principle, a "transverse motion" (normal to the longitudinal direction) is not necessarily produced during the guide motion.

The guide stroke, which as mentioned can be provided relatively large (e.g. several cm), can advantageously be used for example not only to measure the change in length of the sample concerned, which in practice tends to be relatively small, but also, in contrast, a relatively large sample length (e.g. before the start of the actual measurement, i.e. for example the measurement of a change in the sample length).

Provision is made in an embodiment such that the pushrod base comprises a carriage guided directly by the guide device and a pushrod holding fixture which can be connected or is connected directly to the pushrod, wherein the carriage and the pushrod holding fixture are connected to one another by an elastically deformable body.

An advantage of this embodiment consists in the fact that a force to be predetermined or a deformation to be predetermined in the measurement can be "dosed more finely" than in the case of a rigid connection between the carriage and the pushrod holding fixture. The more elastic the deformable body, the greater the traversing path of the carriage required to achieve a determined force or force change, for example in a TMA.

In a development, provision is made such that the force measuring device is constituted as a deformation measuring device for measuring the deformation of the elastic body.

Especially in the case of the TMA, for example, the elastic body thus advantageously has a dual function, i.e. on the one to create or to influence a conversion characteristic for the conversion of the carriage movement into a force exerted on the sample, and on the other hand as a functional component for the force measurement.

With regard to the specific embodiment of such an elastic body also used for the force measurement, recourse can advantageously be taken to suitable designs from the prior art. Such components, i.e. elastic bodies with a force measuring sensor in each case integrated therein or thereon, are known and commercially available for example as "load cells", in particular so-called platform load cells. Such force sensors known per se can be used advantageously in the invention.

The elastic body can be constituted for example by a plastic material or a metallic material, e.g. in the form of a flexure strip, a flexure strut arrangement or also in a "more solid" form such as for example in the form of a cube, wherein all the edge lengths have a length which does not differ substantially (e.g. by less than a factor of 3) from the average edge length (as, for example, in the examples of embodiment described below by reference to the drawings).

When use is made of a cuboid embodiment of the elastic body, in particular when the latter is constituted by a metallic material, it may be of advantage to recess the material for example in a central region in order to obtain a corresponding weakened portion and consequently greater elasticity compared to a solid material.

In a development, provision is made such that a mechanical stop is constituted between the carriage and the pushrod holding fixture, in such a way that a relative movement between the carriage and the pushrod holding fixture and therefore the deformation of the elastic body is limited. Mechanical overloading of the elastic body or of the load cell can thus advantageously be avoided.

In a structurally simple embodiment, provision is made for the implementation of the mechanical stop such that the carriage is constituted or provided with a stop nose projecting from the latter, which at its distal end abuts against a stop face of the pushrod holding fixture when corresponding (maximum permissible) deformation is reached. For this purpose, the distal end of the stop nose can for example engage in a correspondingly dimensioned recess of the pushrod holding fixture. The inverse arrangement is also possible, wherein a stop nose protrudes from the pushrod holding fixture and comes into contact with a distal end with a contact face when corresponding deformation is reached, said stop face being provided on the carriage (e.g. in a corresponding recess).

In an embodiment particularly advantageous for use in a TMA, provision is made such that the drive device comprises a stepping motor, in particular for example a piezo stepping motor, for the stepped adjustability of the pushrod base relative to the stationary base.

A stepping motor offers the advantage, for example, that the control, as part of a software control system of the device, can take place in a straightforward and precise manner.

In an embodiment particularly advantageous for use in a DMA, provision is made such that the drive device comprises an oscillatory motor or actuator, in particular for example a plunger coil arrangement for generating a movement of the pushrod base relative to the stationary base that is oscillatory, in particular changing sinusoidally with time. In a "DMA operation" of the device, a predetermined deformation path amplitude and frequency of the motor operation can then be controlled by means of the control device.

In a preferred embodiment, the control device is constituted as a program-controlled control device, by means of which a control signal used to control the drive device (e.g. stepping motor, plunger coil etc.) is generated during operation of the device.

In the case of a TMA, information (e.g. a digital signal) is inputted into this control device during the measurement, said information being representative of the force detected by the force measuring device, in order to generate the control signal for the drive device on this basis.

In the case of a DMA, information (e.g. a digital signal) is inputted into this control device during the measurement, said information being representative of the movement (e.g. deformation path; or in the case of an oscillatory motion: deformation path amplitude and frequency) determined by means of the path sensor, in order to generate the control signal for the drive device on this basis.

Commercial load cells, which are provided for example with a strain gauge fitted to the elastic body, can supply for example an analog force measurement signal, which can then be fed to the control device having been converted by means of an analog/digital converter. In the case of the "DMA operation", processing of the signal to ascertain the amplitude and frequency or phase shift can be provided, for example before or after such an analog/digital conversion.

With a control program running in the control device, it is then possible to implement the control of the drive device required in the invention, in the case of the "TMA operation" depending on the force detected by means of the force measuring device according to the predetermined force loading, and in the case of the "DMA operation" depending on the deformation detected by means of the path sensor according to the predetermined deformation.

The program-controlled control device can be used to great advantage also in connection with the selection of the force or deformation loading, i.e. in the case of the TMA, for example of a time-dependent variable (alternatively: constant) force curve.

The control device or the control program running on the latter is preferably constituted in such a way that an operator can select a desired force or deformation loading by means of a suitable man-machine interface (e.g. keyboard, monitor etc.). This selection is then used by the control device during the measurement in order to control the drive device depending on the force detected by means of the force measuring device or the deformation detected by means of the path sensor according to the predetermined force or deformation loading.

The control of the drive device provided in a "TMA operation" "depending on the force detected by means of the force measuring device according to the predetermined force loading" can also be termed a control by means of which the force actually exerted on the sample and detected by means of the force measuring device ("actual value") is adjusted using the drive device, in such a way that said force corresponds to the selected force loading, i.e. the selected constant or temporally varying force ("setpoint value").

The same applies to the "DMA operation", in which the actual deformation of the sample (measured with the aid of the path sensor), i.e. an "actual value", is adjusted using the drive device, in such a way that said deformation corresponds to the selected deformation ("setpoint value"), e.g. a deformation path varying over time with a specific amplitude and a specific frequency.

The details of such a control or a specific control characteristic (e.g. P-, PI, PID-control etc.) can be advantageously selected by the aforementioned control program and, if need be, can be influenced by the operator.

In an embodiment, the path sensor, by means of which the movement of the pushrod in the longitudinal direction relative to the base is measured, is constituted by an optical path measurement system. Preferably it is an optical path measurement system operating contactless, so that, advantageously, no force falsifying the measurement result is exerted by the path measurement on the pushrod or a device component connected to the pushrod.

In a development, provision is made such that the optical path measurement system comprises a linear measuring scale and a sensor with connected linear encoder electronics, wherein the linear measuring scale is connected to the pushrod or a part connected thereto in a shear-resistant manner in the longitudinal direction, and the sensor is disposed stationary, or vice versa.

The part connected to the pushrod in a shear-resistant manner in the longitudinal direction can in particular be the aforementioned pushrod holding fixture, which can be connected, preferably by means of the aforementioned elastic body, to a carriage of a guide device constituted as a "linear guide".

The measurement of the pushrod movement by means of the path sensor is preferably provided with a resolution of at most 10 nm, more preferably at most 1 nm, or even at most 0.1 nm.

In the invention, such a path resolution can advantageously be achieved over the entire measurement range of the path sensor (e.g. at least 5 mm, in particular at least 10 mm) (e.g. using a path sensor comprising a linear measuring scale and a sensor, e.g. as described above).

In a development of the device according to the invention, provision is made such that the latter also comprises a sample chamber, which can be temperature-regulated in a controlled manner, with a sample holder provided therein for mounting the sample and, furthermore, the control device is designed to control a predetermined time-dependent temperature regulation of the sample chamber during the measurement. According to this development, the device is thus extended to form a device for performing a thermomechanical analysis (TMA) or a dynamic-mechanical analysis (DMA).

The time-dependent temperature regulation of the sample chamber required for this can advantageously also be controlled by the aforementioned control device.

In the case of the implementation of a TMA device, the control program running in the control device can receive the following in particular as inputs:

beforehand: operator input(s) for the definition of a "TMA measurement program", e.g. time-related course of the temperature-regulation temperature and the force loading, during the measurement: a signal representative of the force detected by means of the force measuring device, during the measurement: a signal representative of the change in length of the sample detected by means of the path sensor, and during the measurement: a signal representative of a temperature detected in the sample chamber and/or directly on the sample (e.g. to bring about a temperature regulation such as is known for TMA devices).

The control program can supply as outputs during the measurement:

a control signal for controlling the temperature regulation of the sample chamber (e.g. by means of an electric heating device), and a control signal for controlling the drive device.

During the TMA measurement, the sample temperature and the change in length of the sample detected by means of the path sensor are recorded in a time-resolved manner.

Diverging from this, in the case of the implementation of a DMA device, the control program running in the control device would receive beforehand one or more operator inputs for the definition of a "DMA measurement program", e.g. time-related course of the temperature-regulation temperature and the desired deformation, and would carry out a control of the drive device according to a "DMA operation" (and not a "TMA operation"). During the DMA measurement, the sample temperature and the deformation force on the sample detected by means of the force measuring device are recorded in a time-resolved manner (wherein "deformation force" preferably means, as already explained, a deformation force amplitude and a deformation force phase shift).

According to a further aspect of the present invention, a method usable for example for the TMA for measuring a change in length of a sample is proposed, wherein this sample is force-loaded in a predetermined manner in a direction, referred to hereinafter as the longitudinal direction, wherein the predetermined force is exerted on the sample by means of a pushrod extending in the longitudinal direction and the movement of the pushrod resulting from the change in length of the sample in the longitudinal direction is measured, and wherein a drive of a pushrod base, to which the pushrod is fixed, takes place in the longitudinal direction relative to a stationary base, wherein this drive takes place depending on the force exerted by the pushrod on the sample and detected by means of the force measuring device according to the predetermined force loading.

According to yet another aspect of the present invention, a method usable for example for the DMA for measuring a deformation force on a sample deformed in a predetermined manner in a direction, referred to hereinafter as the longitudinal direction, wherein the predetermined deformation of the sample is brought about by means of a pushrod extending in the longitudinal direction and the deformation force accompanying the deformation of the sample in the longitudinal direction is measured, and wherein a drive of a pushrod base, to which the pushrod is fixed, takes place in the longitudinal direction relative to a stationary base, wherein this drive takes place depending on the movement brought about by the pushrod on the sample and detected by means of the path sensor according to the predetermined deformation.

The distinctive features or embodiments and developments described above with reference to the two variants of embodiment of the device according to the invention can be provided in an analogous manner, individually or in any combination, also for these two variants of embodiment (for the "TMA operation" or for the "DMA operation") of the method according to the invention.

The use of a device and/or a method of the described type for measuring a change in length of a sample in the context of a TMA device or a TMA method is proposed according to yet another aspect of the present invention.

The use of a device and/or a method of the described type for measuring a deformation force on a sample in the context of a DMA device or a DMA method is proposed according to yet another aspect of the present invention.

With these uses and the measurement methods according to the invention, provision is made according to a development such that, before the measurement of the change in length of the sample or the deformation force on the sample, the length of the sample can also be measured by means of the path sensor. For this purpose, the following sequence can be provided with the invention:

In the first place (without the sample disposed in the device), the control device controls (in response to a corresponding operator input) the traversing of the pushrod in the direction of a sample holding fixture (e.g. a sample holder or a stationary sample stop face), until the end of the pushrod strikes against a stationary face (stop face), against which the sample is subsequently adjacent. The striking can be detected in a straightforward manner by evaluating the measured force (abrupt increase) and/or the path sensor signal (no further change in the path).

The control device then triggers a retraction of the pushrod, so that space for the insertion of the sample is created in the region of the sample holding fixture, wherein the traversing distance during this retraction is detected by means of the path sensor. For many applications, the retraction preferably takes place by at least 1 cm, if appropriate also for example by at least 2 or 3 cm. A maximum traversing path of 5 cm is usually sufficient.

After the sample has then been positioned in such a way that it lies adjacent to the aforementioned stop face, the pushrod is again traversed towards the sample holding fixture or the sample, until the pushrod strikes against the sample (detection again using the force measurement and/or the path distance measurement), wherein the traversing distance required for this is again detected by means of the path sensor.

The difference between the two detected path distances thus provides the information concerning the length of the sample, which can be calculated by the control device and outputted for example for the operator and/or stored in the control device (for subsequent consideration in the evaluation).

BRIEF DESCRIPTION OF THE DRAWINGS

The invention is described in greater detail below with the aid of examples of embodiment making reference to the appended drawings. In the figures.

DETAILED DESCRIPTION OF THE INVENTION

FIGS. 1 to 4 show a first example of embodiment of a device 10 for measuring a change in length of a sample. Device 10 is used in this example in the context of a so-called thermomechanical analysis (TMA) and thus constitutes a component part of a TMA device.

Figure 1:
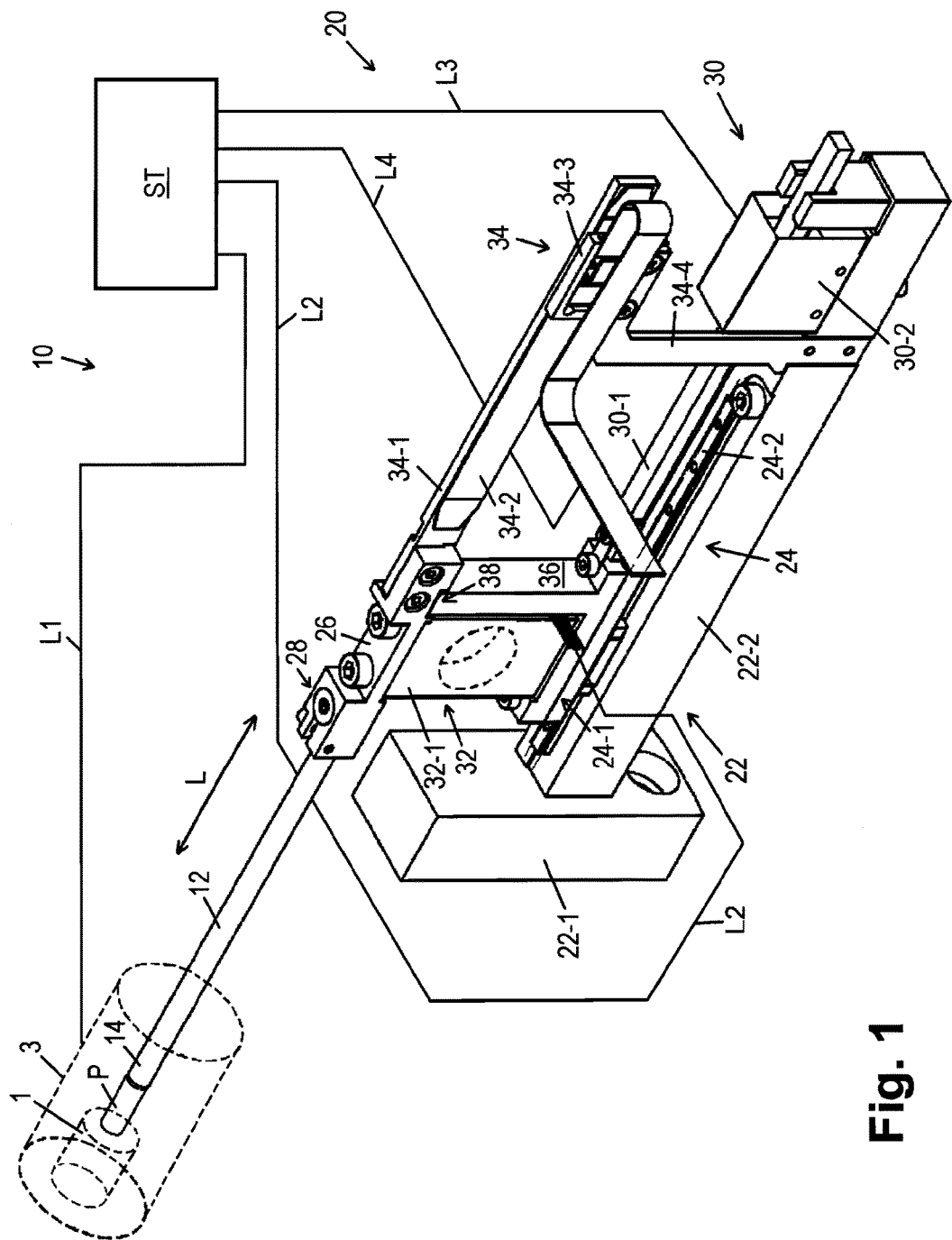
FIG. 1 shows a perspective view of a device for measuring a change in length of a sample according to a first example of embodiment.
Figure 2:
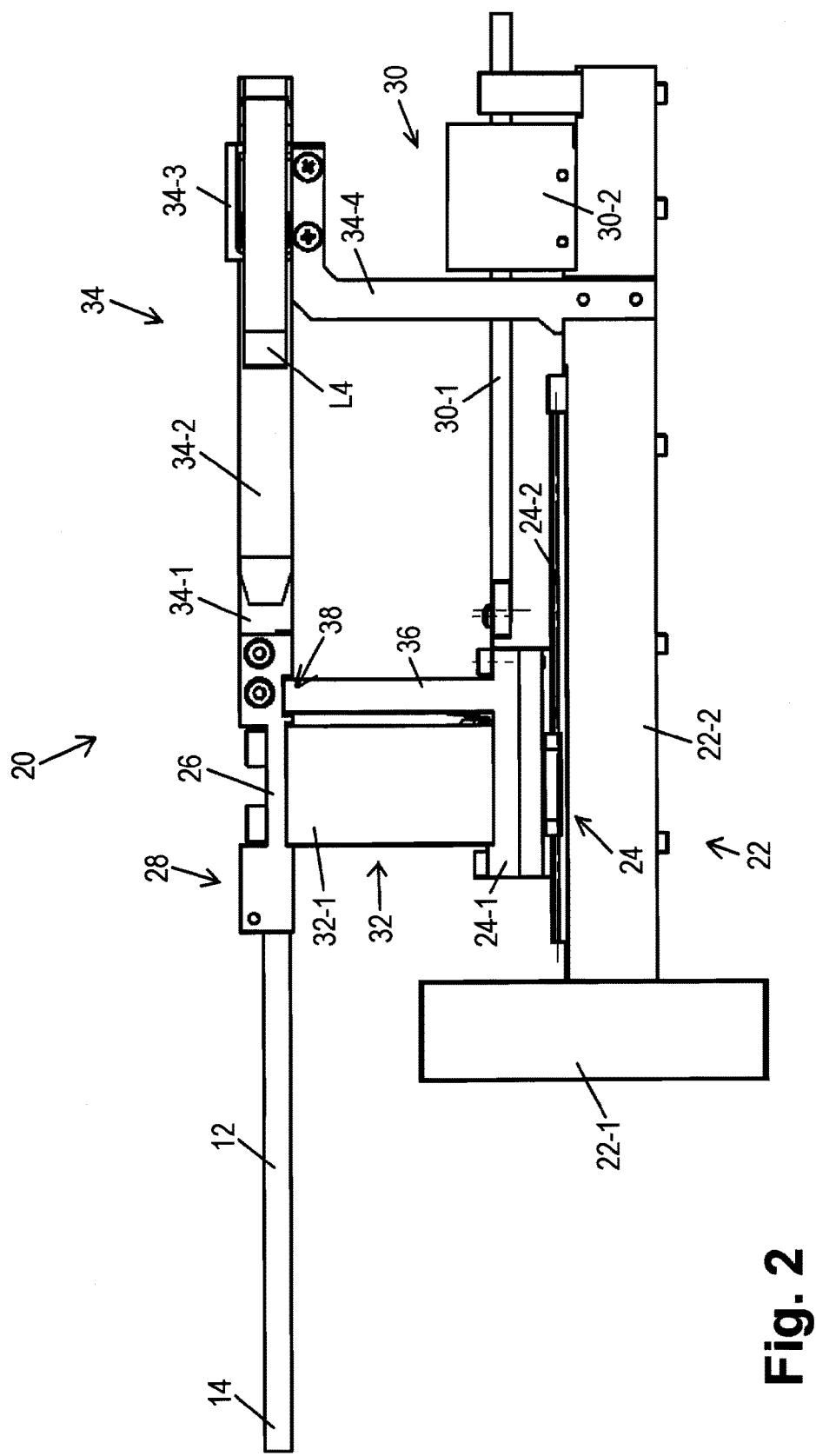
FIG. 2 shows a side view of the device according to the first example.
Figure 3:
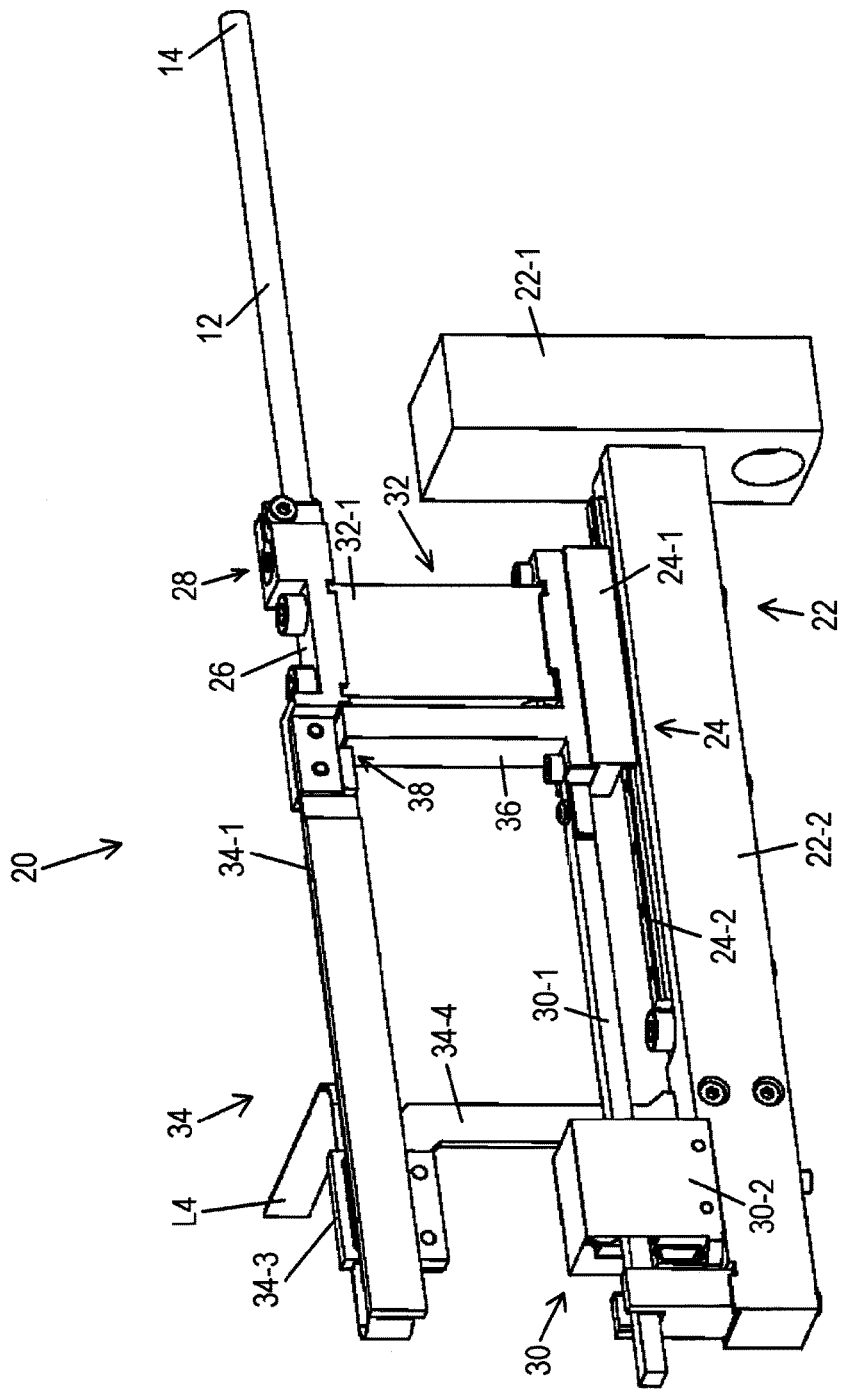
FIG. 3 shows a further perspective view of the device according to the first example.

As further components of the TMA device, the following are represented in FIG. 1 by dashed lines: a sample holder 1 in a furnace 3, which can be temperature-regulated in a controlled manner, for the housing and controllable temperature-regulation of sample P, on which the TMA measurement is to be carried out.

In the measurement, the change in length (here for example resulting from heating or cooling of sample P in furnace 3) is measured in a direction which is referred to hereinafter as the longitudinal direction and is indicated in FIG. 1 by double arrow L. Moreover, sample P is subjected in the measurement to predetermined force loading, which also acts on the sample in longitudinal direction L.

For the example of a TMA measuring device illustrated here, the term "force loading" is understood to mean a time-dependent force which acts on sample P and which is preselected during the length (change) measurement in coordination with a time-related temperature curve ("temperature program").

Device 10 comprises a pushrod 12, which exerts the predetermined force (here: compressive force) on sample P by means of a pushrod end 14 during the measurement.

In this application, the material of the pushrod should have the smallest possible thermal expansion or at least a well defined thermal expansion, so that this thermal expansion has little influence on the measurement result or can be duly taken into account in a control program and/or a subsequent evaluation. The same applies to the material of the pushrod holding fixture.

Moreover, device 10 comprises a measuring device 20, to which pushrod 12 is fitted and by means of which the movement of pushrod 12 resulting from the change in length of sample P in the longitudinal direction L is measured during the measurement. Measuring device 20 comprises:

a stationary base 22, which in the represented example comprises a first base part 22-1 (e.g. for holding furnace 3 with respect to measuring device 20) and a second base part 22-2 extending elongated in longitudinal direction L, a pushrod holding fixture 26 mounted on stationary base 22 so as to be movable relative to stationary base 22 in longitudinal direction L by means of a guide device 24, pushrod 12 being fixed to said pushrod holding fixture 26 in the represented example by means of a screw clamp 28, a controllable drive device 30 for driving pushrod holding fixture 26 in longitudinal direction L relative to stationary base 22, a force measuring device 32 for detecting the force exerted by pushrod 12 on sample P, a control device ST, which is designed to control drive device 30 depending on the force detected by means of force measuring device 32 according to the predetermined force loading (for the sake of simplicity, control device ST is shown only in one of FIGS. 1 to 4 (FIG. 1)), and a path sensor 34 for measuring the movement of pushrod 12 in longitudinal direction L relative to base 22.

The function of represented device 10 can be described as follows:

Proceeding from the situation represented in FIG. 1, wherein sample P is already disposed on sample holder 1 in furnace 3 and is contacted by pushrod end 14 at the end facing away from sample holder 1, a "TMA measurement program" is carried out by means of a control program running in control device ST, said TMA measurement program consisting in heating sample P according to a preselected time-related temperature curve, preloading sample P in a predetermined manner by means of pushrod 12 according to a force program (here: Time-dependent compressive force) and measuring the change in length of sample P in longitudinal direction L resulting therefrom in the course of time.

Control device ST is connected for this purpose via control lines L1, L2, L3 and L4 to corresponding device components. Line L1 serves to transmit a temperature-regulation control signal to furnace 3 or a temperature-regulation device integrated therein (e.g. electric heating). Line L2 serves to transmit a force measurement signal (measured value of the force exerted on sample P) from force measuring device 32 to control device ST. Line L3 serves to transmit a drive control signal to drive device 30. Line L4 serves to transmit a path measurement signal emitted by path sensor 34.

In particular, the time-dependent length change signal transmitted via line L4 is stored in control device ST so as to be available for a corresponding evaluation after completion of the measurement.

During the measurement, control device ST controls, by means of a control of control device 30, the force exerted by means of pushrod 12 on sample P. This functions as follows: Pushrod 12 is, as already mentioned, fitted to pushrod base 26 by means of screw clamp 28, so that a corresponding loading or adjustment of pushrod holding fixture 26 is transmitted directly to pushrod 12 and therefore onward to sample P.

In the represented example, pushrod holding fixture 26 is not driven directly by drive device 30. On the contrary, pushrod holding fixture 26, as can be seen in FIGS. 1 to 4, is connected (here: screwed) to an—in the figures—upper end of elastic body 32-1, the—in the figures—lower end whereof is connected (here: screwed) to a carriage 24-1 of guide device 24, which carriage is guided in longitudinal direction L in a traversing manner on a guide rail 24-2 of guide device 24 and can be correspondingly traversed by means of a thrust rod 30-1 of drive device 30. The distal end of thrust rod 30-1 is screwed to carriage 24-1, as can be seen in the figures. Accordingly, a control of drive device 30, which in the represented example comprises a piezo stepping motor controlled via line L3, first brings about a displacement of thrust rod 30-1 and thus of carriage 24-1 in longitudinal direction L. By means of elastic body 32-1, this carriage movement is converted via pushrod holding fixture 26 and pushrod 12 into a corresponding force or change in force on sample P.

Accordingly, the unit constituted by carriage 24-1, pushrod holding fixture 26 and elastic body 32-1 disposed in between can also be referred to as a drivable "pushrod base", which is mounted on stationary base 22 so as to be movable relative to stationary base 22 in longitudinal direction L by means of guide device 24 and to which pushrod 12 is fixed (or can be fixed). Pushrod base 24-1, 26, 32-1 is driven in longitudinal direction L relative to stationary base 22, as explained, by controllable drive device 30.

Force measuring device 32 is constituted by elastic body 32-1 together with a strain gauge (not represented in the figures) connected to line L2 (e.g. fitted to an outer face of elastic body 32-1).

Especially when elastic body 32-1 is constituted by a metallic material, a material recessed for example at least in a central region can be used instead of a solid material, as is symbolised by dashed lines in FIG. 1 (here: circular recess in a cuboid body). One or more such recesses of the elastic body can also be provided in the case of further examples of embodiment yet to be described below.

By means of force measuring device 32, the force actually exerted on sample P is measured as a function of time during the measurement and preferably fed as an analog/digital-converted signal via line L2 to control device ST (or analog/digital converted in the control device).

The force loading preselected by a corresponding operator input, i.e. the force to be exerted during the measurement on sample P ("setpoint value"), is also stored in control device ST.

By means of the control program running in control device ST, the measured "actual value" of the force is regulated by a corresponding control of drive device 30 to the "setpoint value" preselected by the preselected force loading.

Friction unavoidable in practice in the region of guide device 24 (between carriage 24-1 and guide rail 24-2) advantageously does not lead to a corresponding falsification of the force measurement.

In the represented example of embodiment, the simultaneously performed measurement of the change in length of sample P likewise does not lead to a falsification of the force measurement. The measurement of the change in length in the represented example is carried out as follows: Fitted to pushrod holding fixture 26, the movement whereof in longitudinal direction L corresponds to the change in length of sample P to be measured, is a measuring scale holder 34-1 with a measuring scale 34-2 constituted thereby or, in the represented example, fitted (e.g. bonded) thereto, so that the change in length of sample is transmitted into a corresponding displacement of measuring scale 34-2, which can thus be measured in a straightforward manner.

For this purpose, path sensor 34 also comprises an optical sensor 34-3 held stationary for the measurement of the relative displacement between this sensor 34-3 and measuring scale 34-2. For this purpose, measuring scale 34-2 is provided or constituted for example with line markings distributed equidistantly over its length, which are detected during the passage of measuring scale 34-2 by means of optical sensor 34-3 and linear encoder electronics connected thereto (or integrated therein), in order to obtain a measurement signal representative of the change in length of sample P (the number of the detected markings is a measure of the change in length). This measurement signal is fed via line L4 to control device ST and is stored digitally there for subsequent evaluation as a time-dependent sample length signal.

The linear encoder electronics can be disposed for example in the region of optical sensor 34-3 or alternatively in the region of control device ST.

In the represented example, the stationary holding of optical sensor 34-3 is brought about by a holder 34-4, which on the one hand is connected (here: screwed) to sensor 34-3 and on the other hand is connected (here: screwed) to base 22.

By means of represented device 10, the change in length of sample P force-loaded in a predetermined manner in longitudinal direction L can thus be advantageously measured in a TMA analysis, wherein the predetermined force is exerted on sample P by means of pushrod 12 extending in longitudinal direction L and the movement of pushrod 12 resulting from the change in length of sample P in longitudinal direction L is measured in a contactless manner, wherein a drive of pushrod base 24-1, 26, 32-1, to which pushrod 12 is fixed, takes place in longitudinal direction L relative to stationary base 22, and wherein this drive takes place by means of the control software depending on the force exerted by pushrod 12 on sample P and detected by means of force measuring device 32 according to the predetermined force loading (force control).

Figure 4:
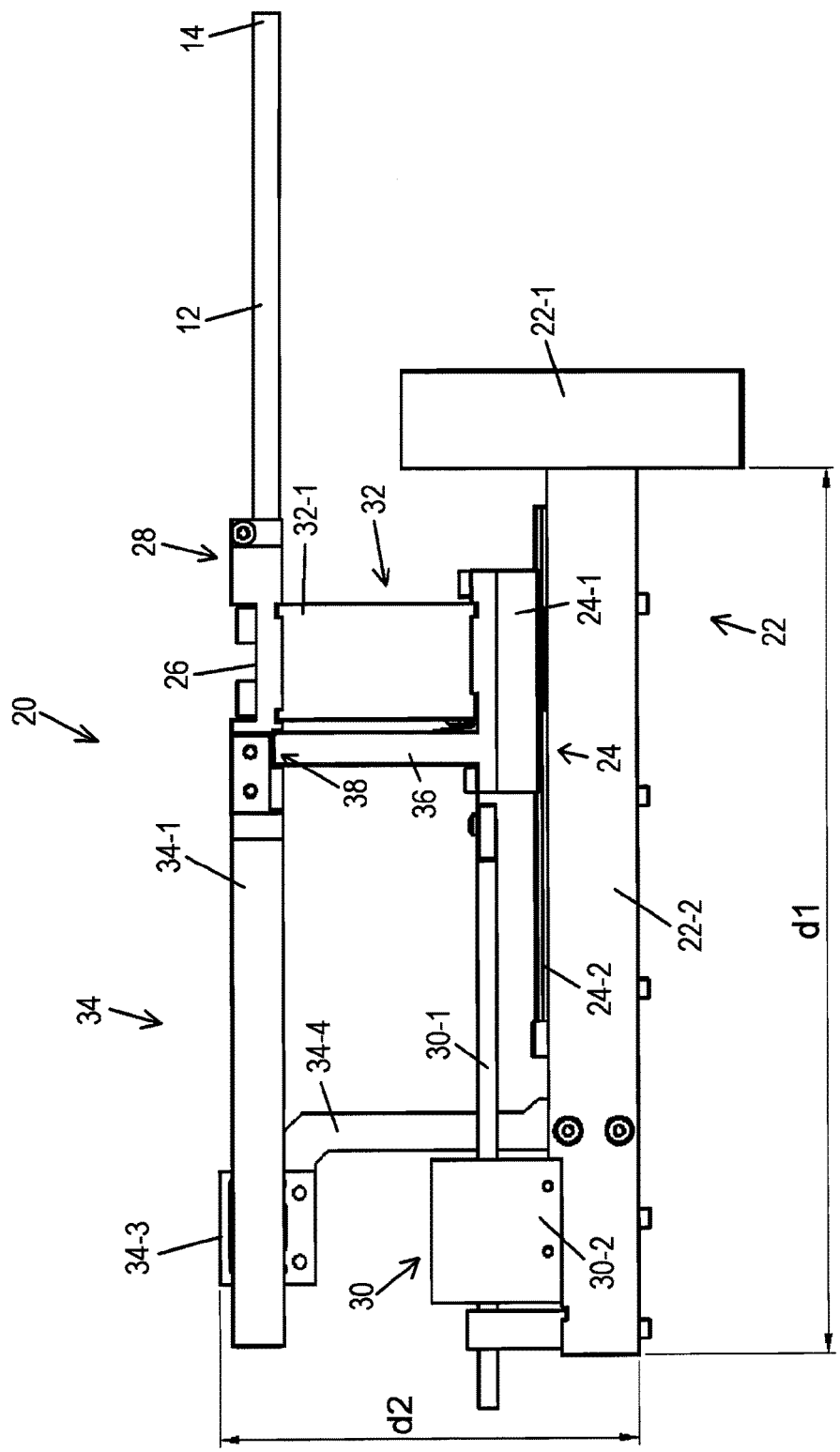
FIG. 4 shows a further side view of the device according to the first example.

In FIG. 4, an overall length (in longitudinal direction L) of measuring device 20 is denoted by d1 and an overall height by d2. Measuring device 20 advantageously has an overall compact structure, in particular an overall width that is very small.

With represented device 10, an "overload protection" is provided for force measuring device 32 and elastic body 32-1 in order to limit the relative movement possibly arising during the operation between carriage 24-1 and pushrod holding fixture 26 and therefore the deformation of elastic body 32-1. In the represented example, this overload protection comprises a stop nose 36 projecting vertically from carriage 24-1 (e.g. constituted integral with a carriage component), said stop nose engaging with its distal end in a stop recess 38 of pushrod holding fixture 26. Viewed in longitudinal direction L, a small clearance between stop nose 36 and the corresponding stop faces constituted by recess 38 arises in each case in the non-deformed state of elastic body 32-1. With a corresponding (maximum permissible) deformation of elastic body 32-1, stop nose 36 abuts against one of these stop faces, so that a further deformation of elastic body 32-1 is prevented.

In the following description of further examples of embodiment, identical reference numbers are used for identically working components, in each case supplemented by a small letter to distinguish the embodiment. Essentially only the differences with respect to the already described example or examples of embodiment will be dealt with and, moreover, reference is thus expressly made to the description of the preceding examples of embodiment.

Figure 5:
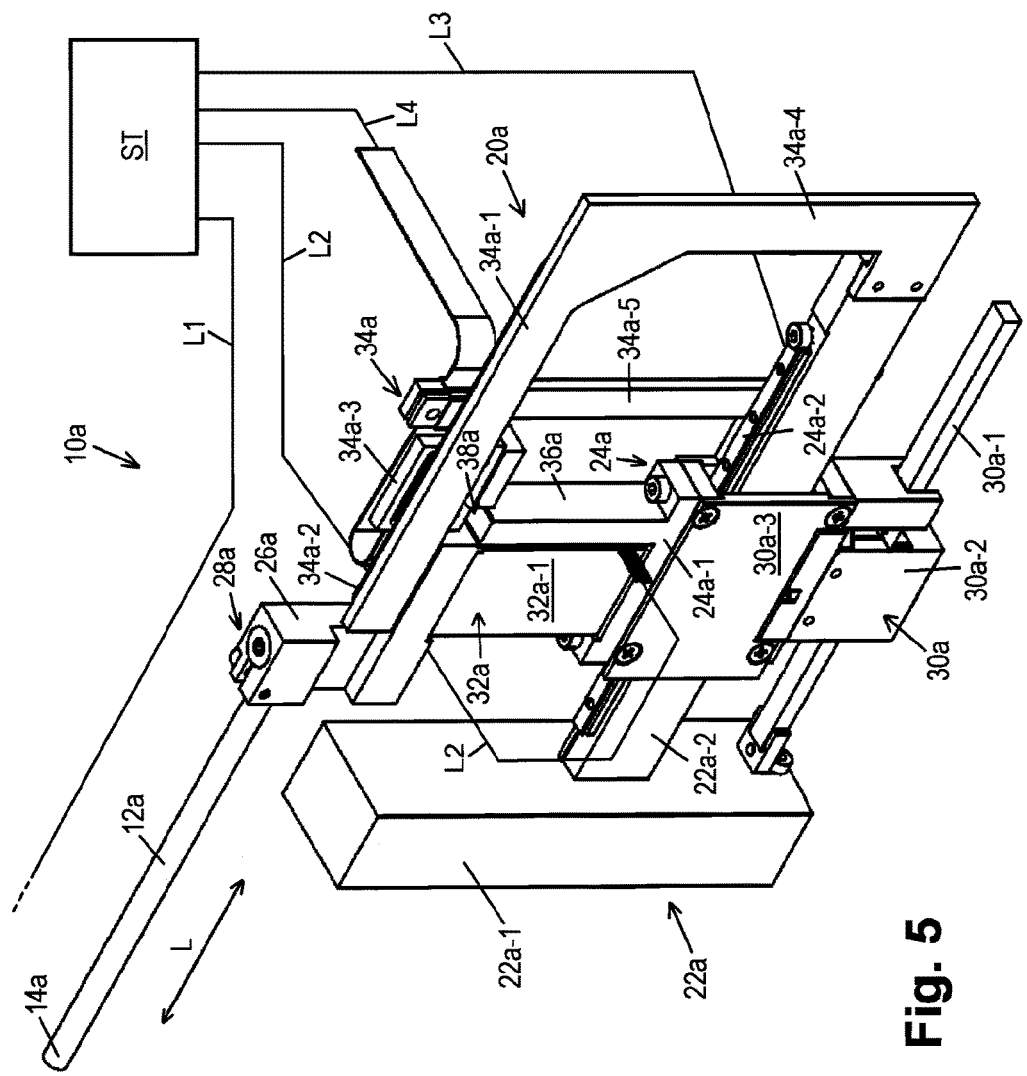
FIG. 5 shows a perspective view of a device for measuring a change in length of a sample according to a second example of embodiment.
Figure 6:
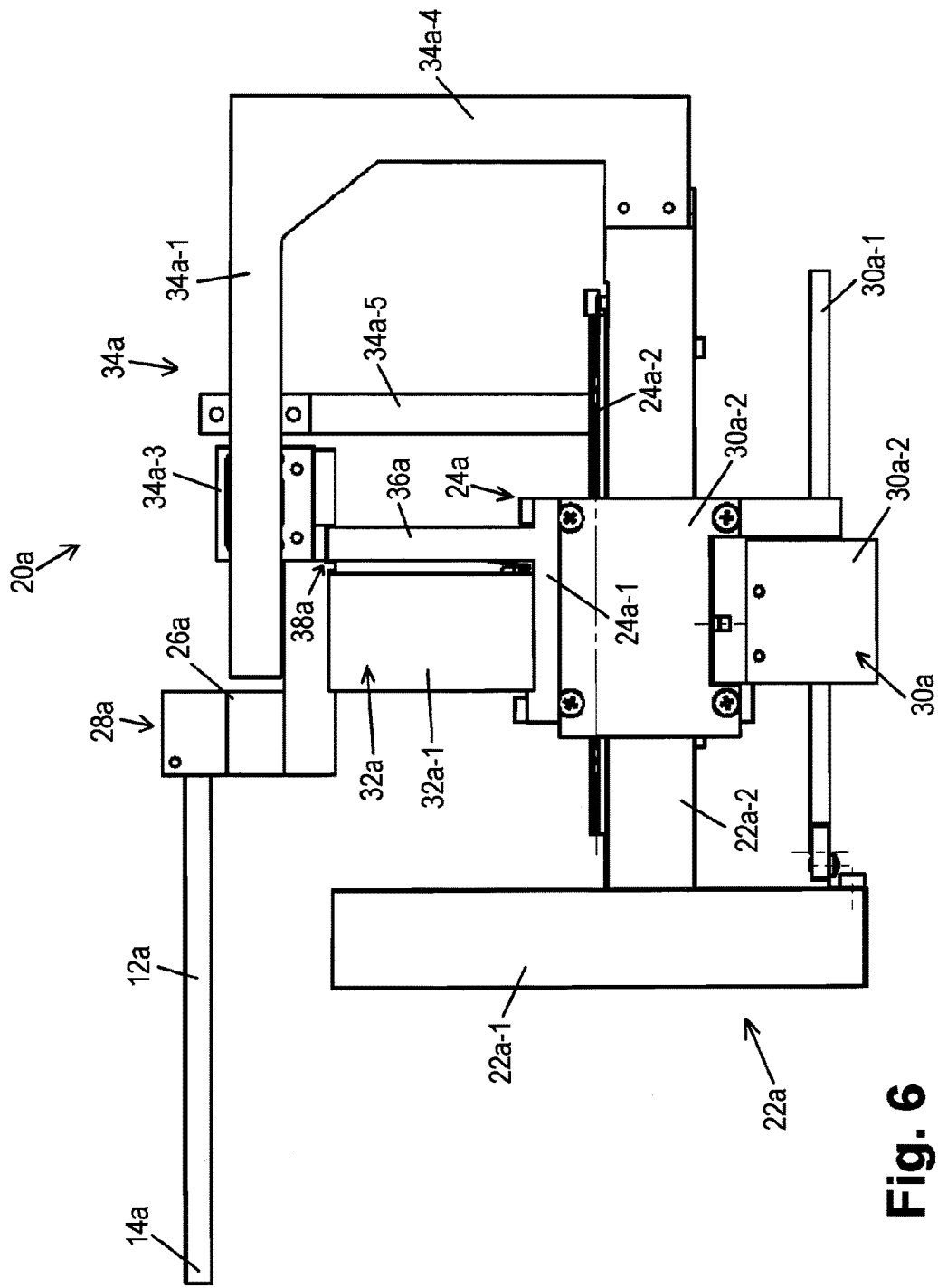
FIG. 6 shows a side view of the device according to the second example.
Figure 7:
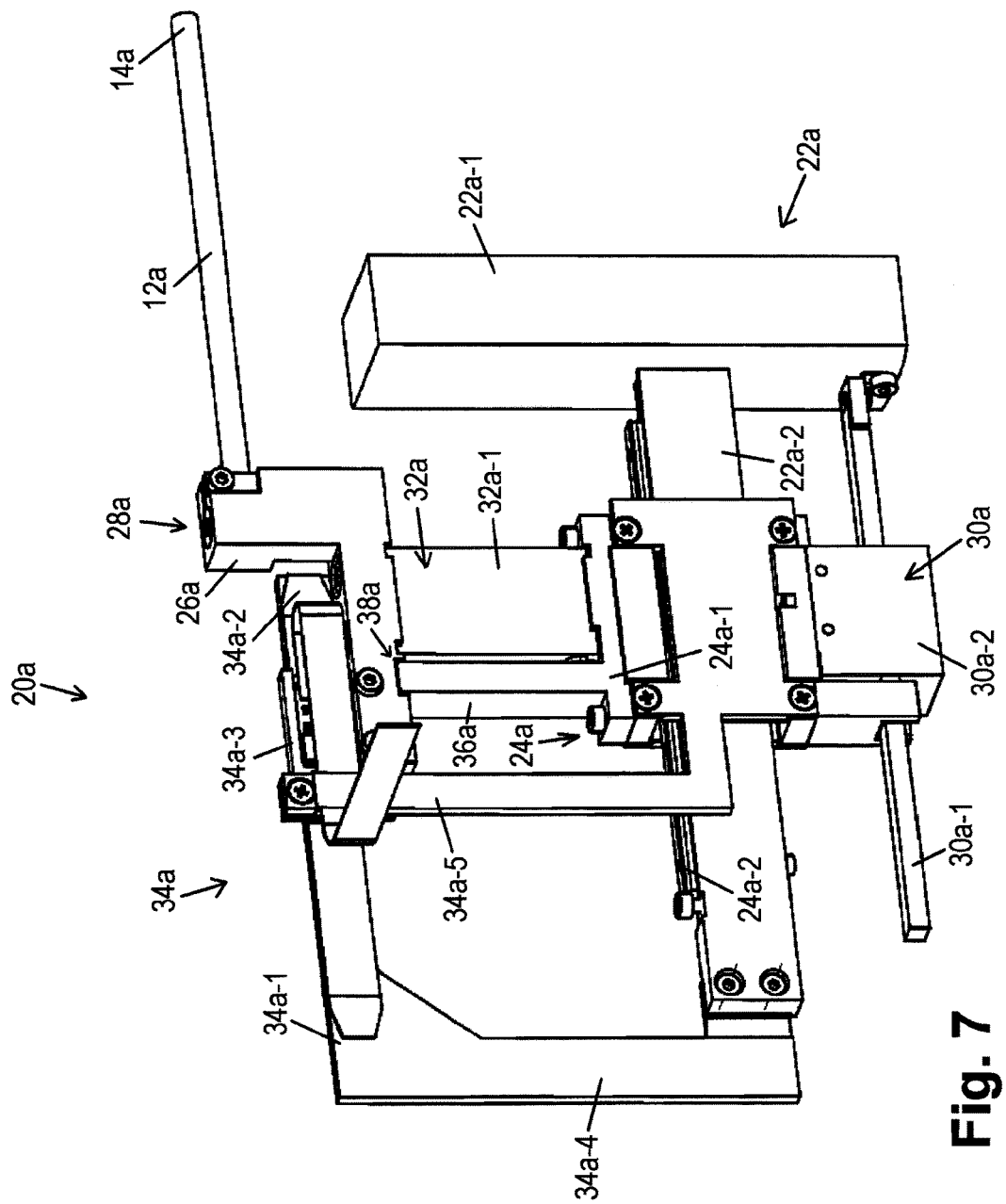
FIG. 7 shows a further perspective view of the device according to the second example.

FIGS. 5 to 8 show a second example of embodiment of a device 10a for measuring a change in length of a sample. For the sake of simplicity, an associated control device ST together with a line arrangement is again shown only in one of these figures (FIG. 5).

In contrast with the already described example of embodiment according to FIGS. 1 to 4, device 10a according to FIGS. 5 to 8 is modified at two points, i.e.
on the one hand, in the region of a guide device 24a, by means of which a pushrod base (carriage 24a-1, pushrod holding fixture 26a and elastic body 32a-1) is mounted so as to be movable in longitudinal direction L relative to a stationary base 22a, and
on the other hand, in the region of the pushrod base or of a path sensor 34a linked thereto for measuring the movement of a pushrod 12a in longitudinal direction L relative to base 22a.

These two modifications which, diverging from the represented example, could in each case also be used as such for modifying the already described example of embodiment, are described in greater detail below.

The modification in the region of the guide device 24a consists in the fact that a piezo stepping motor 30a-2 is held not stationary (i.e. on base 22a), but rather traverses (or "rides") on an associated thrust rod 30a-1, which is connected (here: screwed) fixedly to base 22a. Accordingly, when the employed drive (here: piezo stepping motor 30a-2) is triggered, it is not thrust rod 30a-1 that is moved, but rather drive 30a-2 itself. For the transmission of this movement to carriage 24a-1 of guide device 24a, therefore, piezo stepping motor 30a-2 or its housing is connected by a pair of connecting plates 30a-3 to piezo stepping motor 30a-2 (here: by means of screwed joints). An advantage of this modification consists in the fact that an overall length d1 (see FIG. 8) can be dimensioned smaller compared to the first example of embodiment.

The modification with regard to measuring the movement of pushrod 12a consists in the fact that a linear measuring scale 34a-2 of path sensor 34a is disposed stationary (relative to base 22a) and an optical sensor 34a-3 is disposed "co-traversing" with pushrod 12a or pushrod holding fixture 26a, and not vice versa (as in the first example of embodiment). For this purpose, a holder 34a-4 connected to stationary base 22a supports a measuring scale carrier 34a-1 together with measuring scale 34a-2 disposed thereon, wherein this holder 34a-4 is constituted integral with measuring scale carrier 34a-1 in the represented example. In order to implement the shear-resistant connection between optical sensor 34a-3 and pushrod holding fixture 26a, a fixed connection (here: a screwed joint) is provided between these two components. Moreover, as also represented in FIGS. 5 to 8, a further holder 34a-5 should expediently also be provided, which for example on the one hand can be connected to one of connecting plates 30a-3 (e.g. in one piece) and on the other hand supports a section of line L2 constituted as a flat ribbon cable in the sense of a "strain relief" in a stationary manner relative to carriage 24a-1. Otherwise, there would be the risk of a force acting in an uncontrolled manner via line L2 taking effect on pushrod holding fixture 26a and thus falsifying the force measurement.

Figure 9:
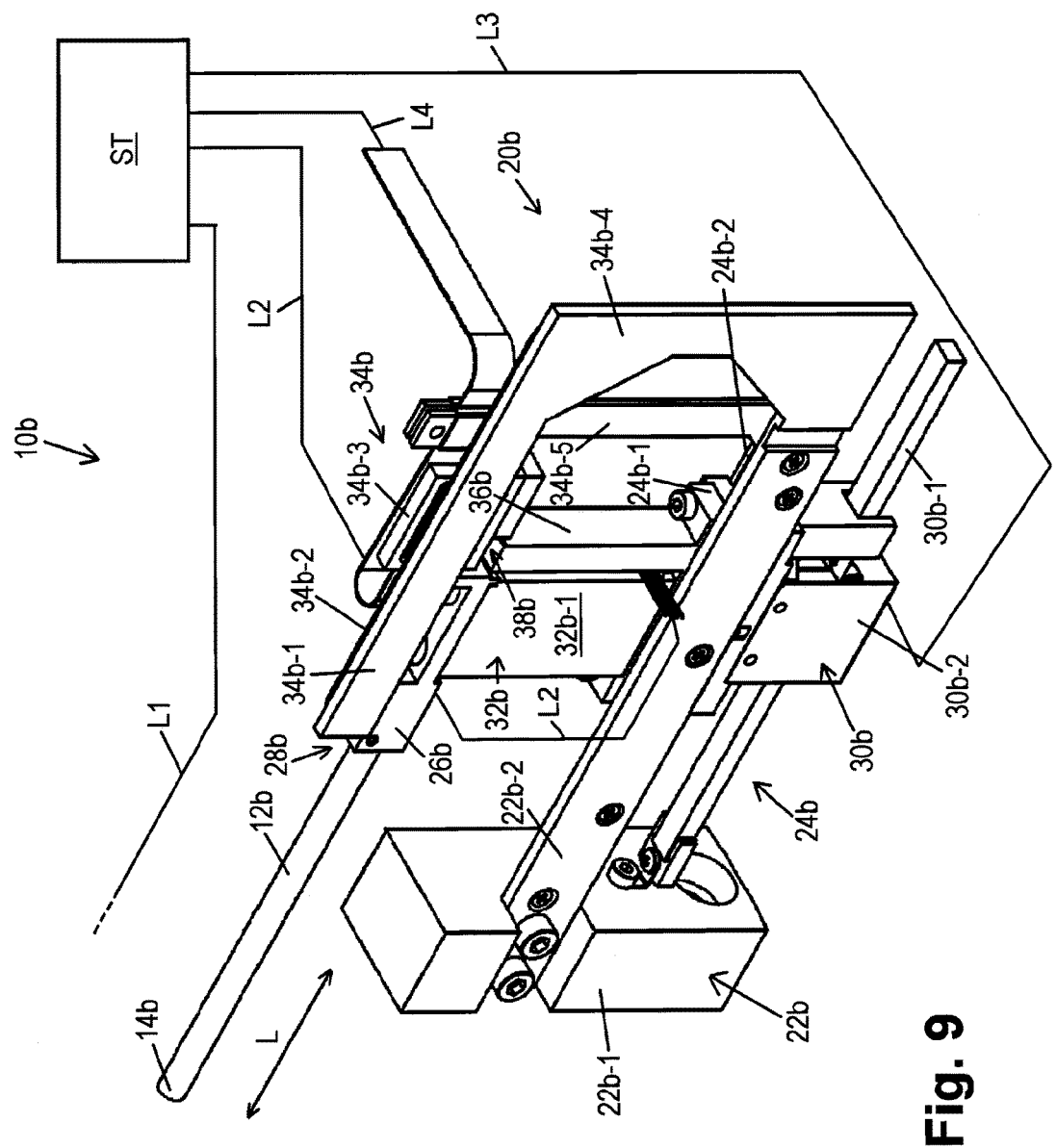
FIG. 9 shows a perspective view of a device for measuring a change in length of a sample according to a third example of embodiment.
Figure 10:
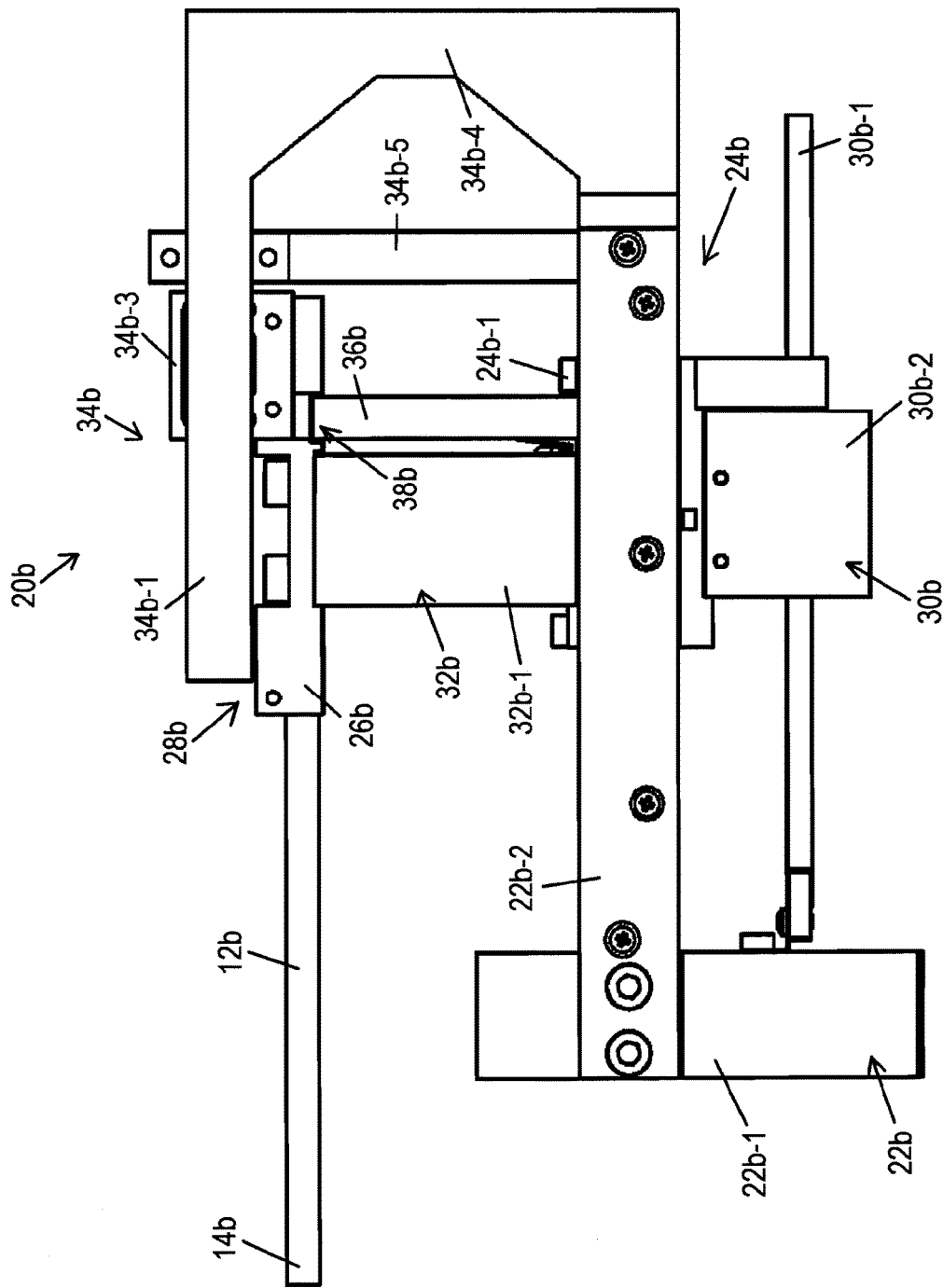
FIG. 10 shows a side view of the device according to the third example.
Figure 11:
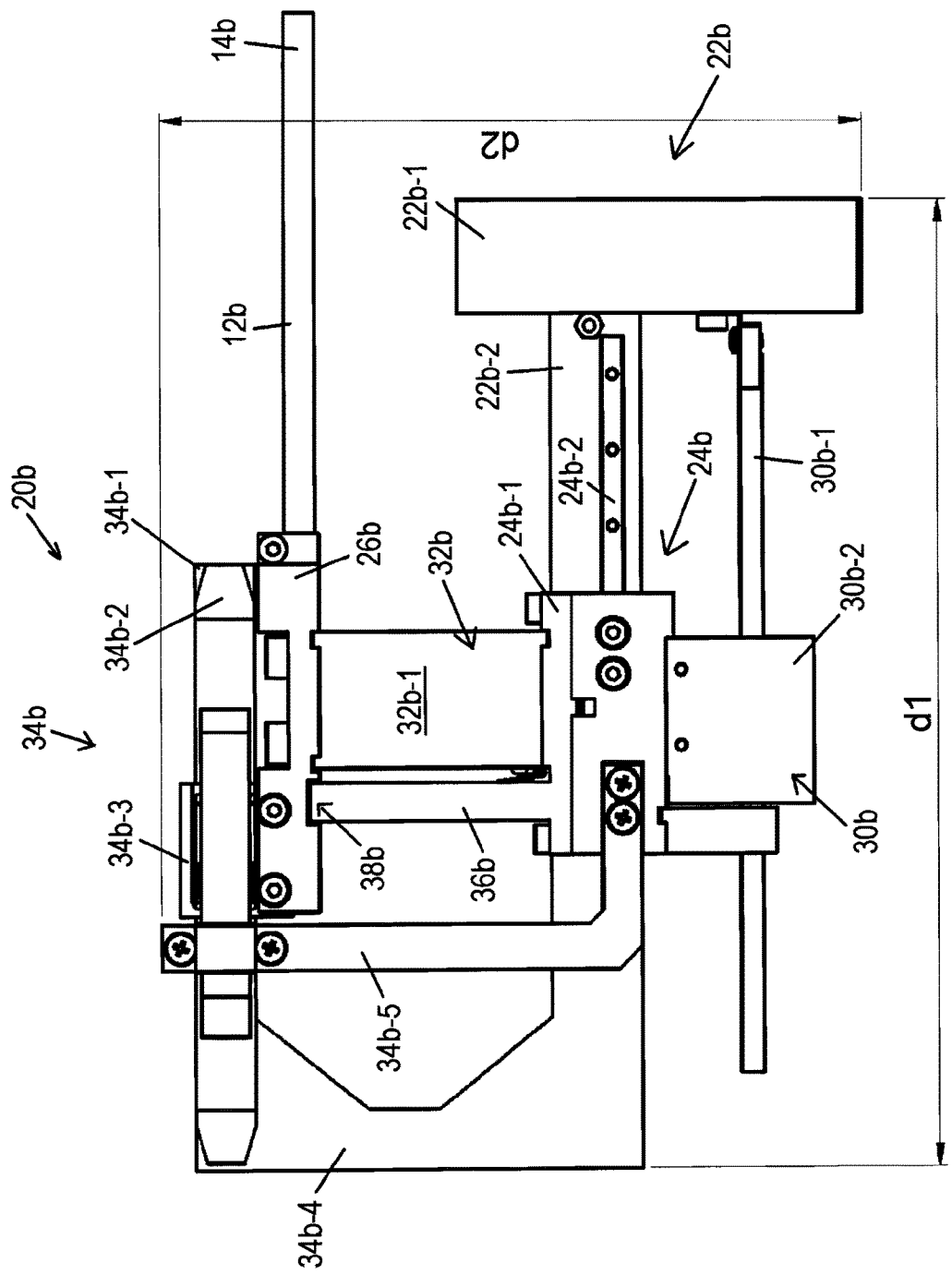
FIG. 11 shows a further side view of the device according to the third example.

FIGS. 9 to 11 show a third example of embodiment of a device 10b for measuring a change in length of a sample. An associated control device ST together with a line arrangement is again shown only in one of the figures (FIG. 9).

In contrast with the already described second example of embodiment (FIGS. 5 to 8), device 10b according to FIGS. 9 to 11 is modified in the region of a guide device 24b for the mobile support of a pushrod base or pushrod holding fixture 26b in longitudinal direction L relative to a stationary base 22b.

In contrast with the second example of embodiment, a guide rail 24b-2 is disposed orientated rotated through 90° (around its longitudinal axis). Guide rail 24b-2 accordingly projects, in FIGS. 9 to 11, in a horizontal direction from a holding part 22b-2 of base 22b extending in longitudinal direction L. Holding part 22b-2 is advantageously constituted as a relatively thin, vertically orientated sheet metal part.

Figure 8:
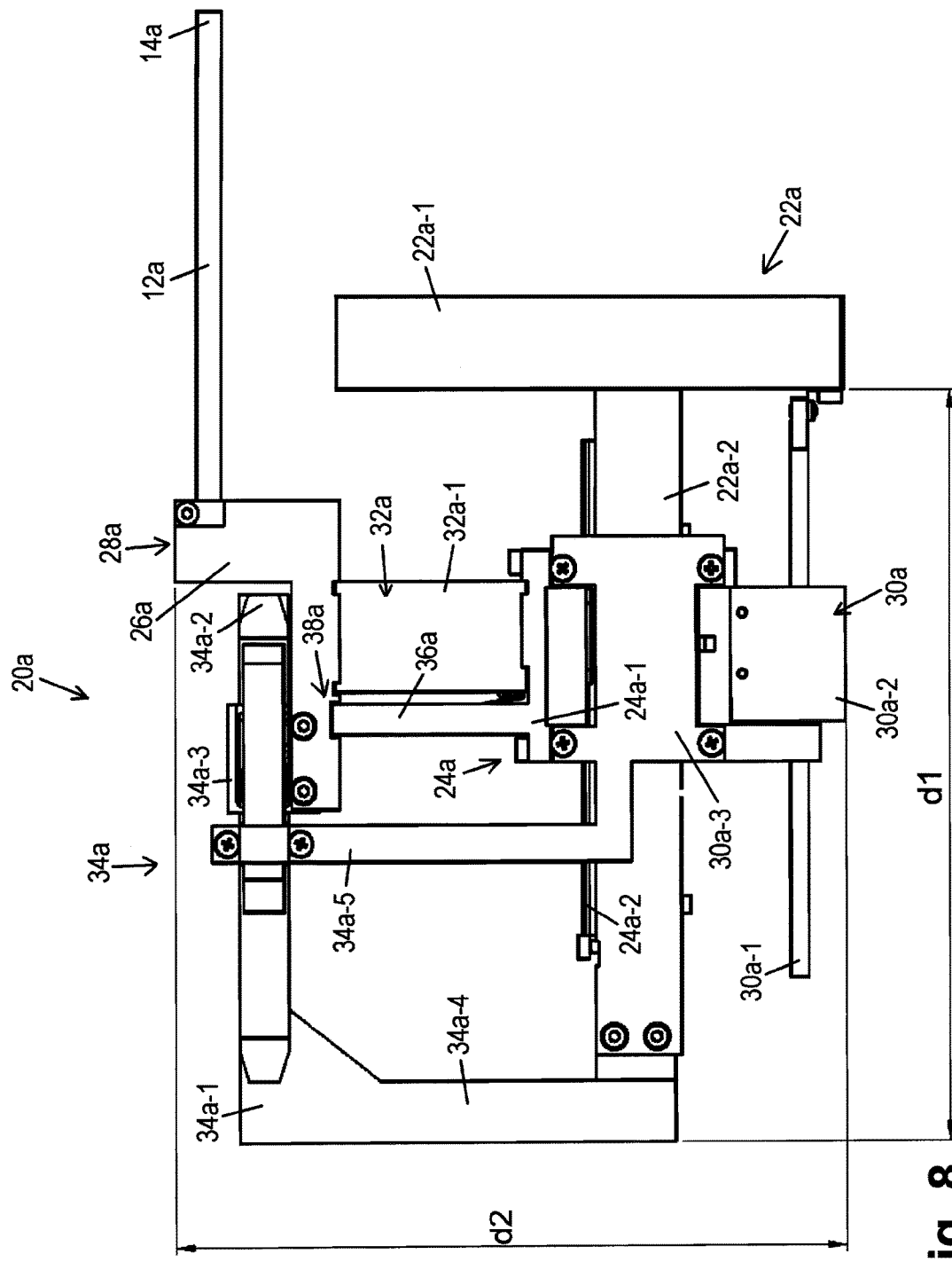
FIG. 8 shows a further side view of the device according to the second example.

In this embodiment, overall height d2 (see FIG. 11) can advantageously be reduced compared to the second embodiment (see FIG. 8).

The shear-resistant connection in longitudinal direction L between drive motor 30b-2 of a drive device 30b on the one hand and a carriage 24b-1 of guide device 24b on the other hand advantageously does not require an arrangement of connecting plates engaging around holding part 22b-2 extending in longitudinal direction L (as in the embodiment according to FIGS. 5 to 8). On the contrary, in the case of device 10b, a direct connection (e.g. screwed joint) is provided between drive motor 30b-2 and carriage 24b-1.

Figure 12:
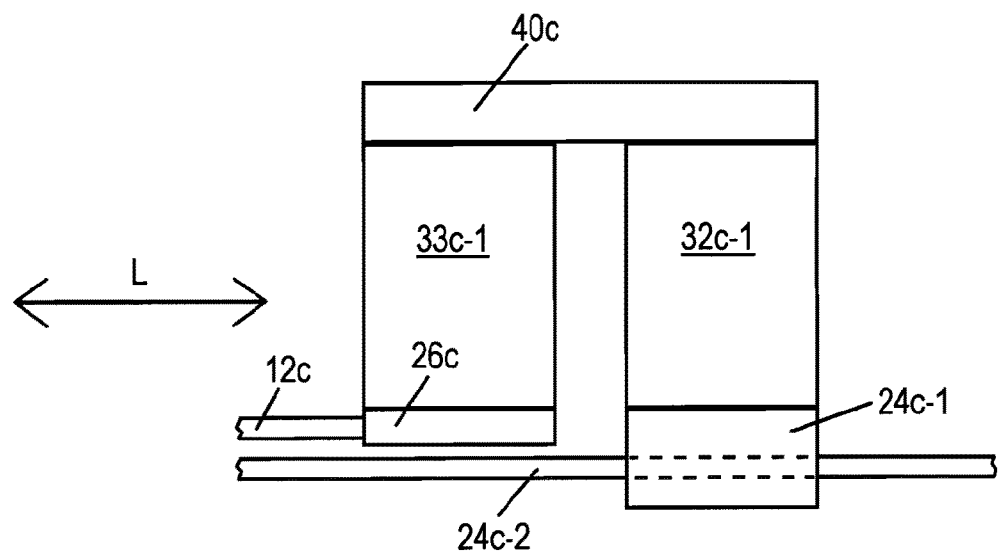
FIG. 12 shows a diagrammatic representation to illustrate a deflection-compensating "series arrangement" of plastic bodies for use in a device for measuring a change in length of a sample.
Figure 13:
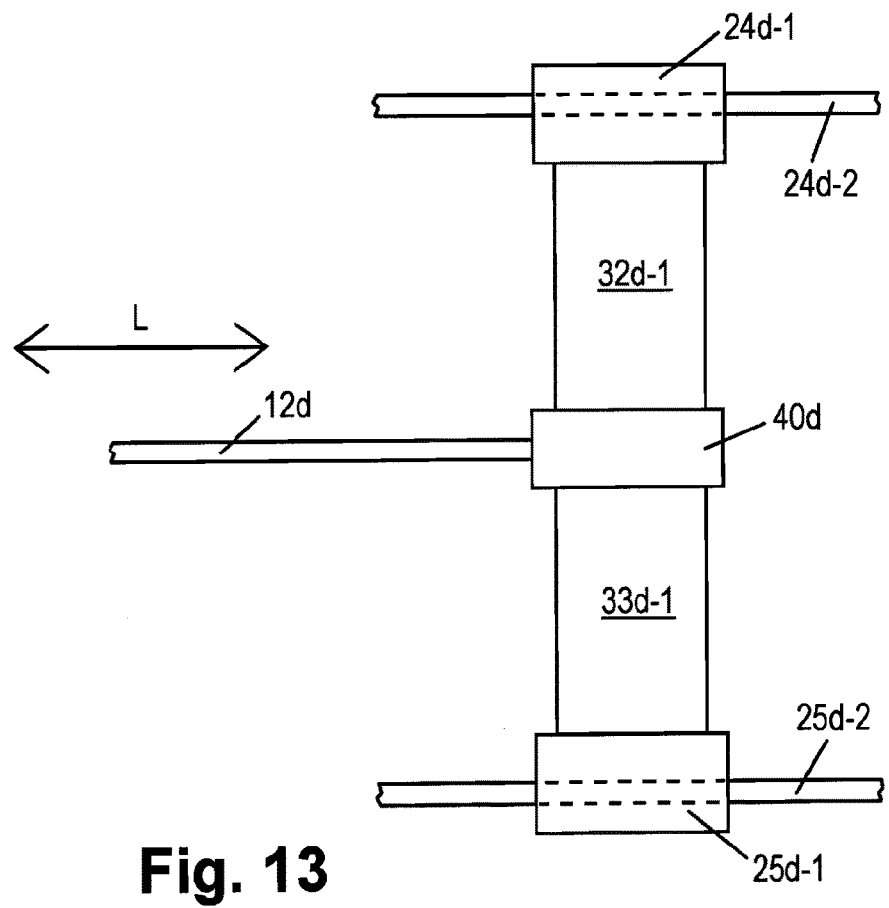
FIG. 13 shows a diagrammatic representation to illustrate a deflection-compensating "parallel arrangement" of elastic bodies for use in a device for measuring a change in length of a sample.

FIGS. 12 and 13 are diagrammatic representations to illustrate two variants of embodiment of a detail of a measuring device of the type described here. This detail described in greater detail below can thus be used in particular to modify the examples of embodiment described above (devices 10, 10a and 10b).

In the examples of embodiment described above, the pushrod base in each case comprises an elastic body (32-1, 32a-1 and 32b-1), which on one side (bottom in the figures) is connected to a carriage guided directly by the guide device and on the opposite side (top in the figures) is connected to the pushrod holding fixture of the pushrod base. During the operation, depending on the adjusted force, a more or less pronounced deformation of the elastic body and a corresponding relative displacement of the pushrod holding fixture relative to the carriage in longitudinal direction L occurs. Depending on the embodiment (shape and arrangement) of the elastic body, however, an albeit very small relative displacement between the pushrod holding fixture and the carriage also occurs normal to longitudinal direction L. Such a transverse displacement is generally undesirable. In order to eliminate this transverse displacement, the modification illustrated in FIGS. 12 and 13 can be used.

The variants of embodiment of FIGS. 12 and 13 have in common the fact that two elastic bodies in a "series arrangement" (FIG. 12) or in a "parallel arrangement" (FIG. 13) are used as a connecting member between the pushrod holding fixture and the carriage, in such a way that their individual contractions or expansions in the transverse direction occurring during the operation mutually compensate for one another at least partially, in particular essentially completely.

FIG. 12 illustrates the first variant, wherein a carriage 24c-1 is guided in longitudinal direction L on a guide rail 24c-2 constituted on the stationary base or fixedly connected to this base and is connected to a side (bottom in FIG. 12) of a first elastic body 32c-1. An opposite second side (top in FIG. 12) of elastic body 32c-1 is connected via a connecting member 40c to a side (top in FIG. 12) of a second elastic body 33c-1. An opposite side (bottom in FIG. 12) of second elastic body 33c-1 is connected to a pushrod holding fixture 26c, to which a pushrod 12c is fixed (or can be fixed).

When the arrangement according to FIG. 12 is used in a measuring device of the type described here, e.g. in one of devices 10, 10a and 10b of the type described in greater detail above, a compensation of the contractions or expansions of the two elastic bodies 32c-1 and 33c-1 occurring during the operation advantageously occurs, so that the relative displacement between the respective pushrod holding fixture 26c and therefore pushrod 12c on the one hand and the respective carriage 24c-1 on the other hand is ultimately essentially limited to a displacement in longitudinal direction L.

For a compensation of the transverse movements that is advantageously as complete as possible, provision can be made for example such that elastic bodies 32c-1 and 33c-1 are constituted essentially identical.

The variant of embodiment according to FIG. 13 differs from the variant according to FIG. 12 solely in that, instead of a "series arrangement" of two elastic bodies 32c-1 and 33c-1, a "parallel arrangement" of elastic bodies 32d-1 and 33d-1 is provided.

A guide device in FIG. 13 comprises for this purpose two carriages 24d-1 and 25d-1, which are each guided in longitudinal direction L on an associated guide rail 24d-2 and respectively 25d-2 and are each connected to a first side of elastic body 32d-1 and respectively 33d-1. The other sides of elastic bodies 32d-1 and 33d-1 are connected to one another by connecting member 40d, to which a pushrod 12d is fixed (or can be fixed). The variant according to FIG. 13 also advantageously leads to a compensation of the transverse movements occurring on the individual elastic bodies during the operation.

Although, in the examples according to FIGS. 12 and 13, the two "elastic bodies" are provided as separate components, the latter can, diverging therefrom, also be constituted for example connected in one piece. In the example according to FIG. 12, components 32c-1, 33c-1 and 40c would then be embodied by a suitably shaped elastic body (and in the example according to FIG. 13, components 32d-1, 33d-1 and 40c).

Moreover, diverging from the specific examples according to FIGS. 12 and 13, more than two "elastic bodies" in a series arrangement (see FIG. 12) or in a parallel arrangement (see FIG. 13) could also be used (and, if appropriate, be embodied by a single suitably shaped component).

The examples of embodiment of measuring devices 10, 10a, 10b described above (if applicable, with one of the modifications illustrated in FIGS. 12 and 13) are based on a quite generally advantageous "arrangement principle" of the device components within the scope of the invention, which can be described as follows:

The device has, corresponding to the extension direction of the pushrod, a longitudinal direction (longitudinal direction L), in which, in the extension of a pushrod axis, the pushrod holding fixture (or pushrod base) and the path sensor are disposed in succession, wherein a guide device (preferably according to the "guide rail" principle) extending elongated in the longitudinal direction is likewise disposed in succession in this longitudinal direction, but offset in parallel (in the figures of the examples of embodiment, offset vertically downwards), and wherein the aforementioned elastic body or the force measuring device constituted thereby is preferably housed in the space (offset space) between these two device regions running in the longitudinal direction. An overall very compact device is thus created.

There are two preferred arrangement points for the arrangement of the drive device. On the one hand, the drive device can follow, as in the example according to FIGS. 1 to 4, the guide device in the longitudinal direction and can act, for example with the aforementioned thrust rod, on a carriage of the guide device. On the other hand, the drive device can be disposed, as for example in the examples according to FIGS. 5 to 8 and FIGS. 9 to 11, with an offset normal to the longitudinal direction relative to the guide device, for example on the side of the guide device facing away from the pushrod holding fixture.

Although the examples of embodiment of devices 10, 10a and 10b described above have been described for use in a TMA device, it is understood that the latter could in principle also be used in a DMA device by suitable modification of the control device or of the control software running thereon (if need be, by adaptation/optimisation of still further details, such as for example the use of a plunger coil arrangement instead of the piezo stepping motor).

With a device (e.g. TMA or DMA device or dilatometer) created with the device according to the invention, the "longitudinal direction" of the device can be orientated for example vertically (e.g. preferably for a TMA and DMA device) or for example horizontally (e.g. preferably for a dilatometer).

What is claimed is:

1. A device for measuring a change in length of a sample force-loaded in a predetermined manner in a longitudinal direction, with a pushrod extending in the longitudinal direction, which exerts a predetermined force on the sample with an end of the pushrod during the measurement, and with a measuring device by which, during the measurement, the movement of the pushrod resulting from the change in length of the sample in the longitudinal direction is measured, wherein the measuring device comprises:
   a stationary base;
   a pushrod base to which the pushrod is configured to be fixed, the pushrod base mounted on the stationary base by a guide device so as to be movable in the longitudinal direction relative to the stationary base;
   a controllable drive device for driving the pushrod base in the longitudinal direction relative to the stationary base;
   a force measuring device constituted as a deformation measuring device for measuring the deformation of an elastically deformable body, said force measuring device configured to detect the force exerted by the pushrod on the sample;
   a path sensor disposed relative to the to the pushrod for measuring the movement of the pushrod in the longitudinal direction relative to the base; and
   a control device to control the controllable drive device depending on the force detected by the force measuring device according to the predetermined force loading;
   wherein the pushrod base comprises a carriage guided directly by the guide device and a pushrod holding fixture which is configured to be connected directly to the pushrod, wherein the carriage and the pushrod holding fixture are connected to one another by the elastically deformable body.

2. The device according to claim 1, wherein the control device is designed, according to an operating mode, to provide a constant force loading or deformation of the sample throughout an entirety of the measurement.

3. The device according to claim 1, wherein the control device is designed, according to an operating mode, to provide a variable force loading or deformation of the sample during the measurement.

4. The device according to claim 1, wherein a mechanical stop is constituted between the carriage and the pushrod holding fixture, in such a way that a relative movement between the carriage and the pushrod holding fixture and therefore the deformation of the elastically deformable body is limited.

5. The device according to claim 1, wherein the drive device comprises a stepping motor for a stepped adjustability of the pushrod base relative to the stationary base.

6. The device according to claim 1, wherein the path sensor is constituted by an optical path measuring system.

7. The device according to claim 6, wherein the optical path measurement system comprises a linear measuring scale and a sensor with connected linear encoder electronics, wherein the linear measuring scale is disposed on the pushrod or a part connected thereto in a shear-resistant manner in the longitudinal direction, and the sensor is disposed stationary, or vice versa.

8. The device according to claim 1, wherein the device also comprises a sample chamber, which is configured to be temperature-regulated in a controlled manner, with a sample holder provided therein for mounting the sample and, furthermore, the control device is designed to control a predetermined time-dependent temperature regulation of the sample chamber during the measurement.

9. A device for measuring a deformation force on a sample deformed in a predetermined manner in a longitudinal direction with a pushrod extending in the longitudinal direction, which brings about the predetermined deformation of the sample with an end of the pushrod during the measurement, and with a measuring device by which, during the measurement, the deformation force accompanying the deformation of the sample in the longitudinal direction is measured, wherein the measuring device comprises:
 a stationary base;
 a pushrod base to which the pushrod is configured to be fixed, the pushrod base mounted on the stationary base by a guide device so as to be movable in the longitudinal direction relative to the stationary base;
 a controllable drive device for driving the pushrod base in the longitudinal direction relative to the stationary base;
 a force measuring device constituted as a deformation measuring device for measuring the deformation of an elastically deformable body, said force measuring device configured to detect the force exerted by the pushrod on the sample;
 a path sensor disposed relative to the pushrod for measuring the movement of the pushrod in the longitudinal direction relative to the base; and
 a control device to control the controllable drive device depending on the movement detected by the path sensor according to the predetermined deformation;
 wherein the pushrod base comprises a carriage guided directly by the guide device and a pushrod holding fixture which is configured to be connected directly to the pushrod, wherein the carriage and the pushrod holding fixture are connected to one another by the elastically deformable body.

10. A method for measuring a change in length of a sample which is force-loaded in a predetermined manner in a longitudinal direction wherein a predetermined force is exerted on the sample by a pushrod extending in the longitudinal direction and the movement of the pushrod resulting from the change in length of the sample in the longitudinal direction is measured by a path sensor, and wherein a drive of a pushrod base, to which the pushrod is fixed, takes place in the longitudinal direction relative to a stationary base, wherein the drive of the pushrod base takes place depending on the force exerted by the pushrod on the sample and detected by a force measuring device according to the predetermined force loading;
 wherein the pushrod base comprises a carriage guided directly by a guide device and a pushrod holding fixture which is configured to be connected directly to the pushrod, wherein the carriage and the pushrod holding fixture are connected to one another by an elastically deformable body; and
 wherein the force measuring device is constituted as a deformation measuring device for measuring the deformation of the elastically deformable body.

11. A method for measuring a deformation force on a sample deformed in a predetermined manner in a longitudinal direction wherein a predetermined deformation of the sample is brought about by a pushrod extending in the longitudinal direction and the deformation force accompanying the deformation of the sample in the longitudinal direction by a force measuring device is measured, and wherein a drive of a pushrod base, to which the pushrod is fixed, takes place in the longitudinal direction relative to a stationary base, wherein the drive of the pushrod base takes place depending on the movement brought about by the pushrod on the sample and detected by a path sensor according to the predetermined deformation;
 wherein the pushrod base comprises a carriage guided directly by a guide device and a pushrod holding fixture which is configured to be connected directly to the pushrod, wherein the carriage and the pushrod holding fixture are connected to one another by an elastically deformable body; and
 wherein the force measuring device is constituted as a deformation measuring device for measuring the deformation of the elastically deformable body.

* * * * *